United States Patent
Bauer et al.

(10) Patent No.: US 12,376,821 B2
(45) Date of Patent: Aug. 5, 2025

(54) METHOD AND APPARATUS FOR GENERATING A COMBINED THREE-DIMENSIONAL ULTRASOUND IMAGE

(71) Applicant: PIUR IMAGING GMBH, Vienna (AT)

(72) Inventors: Robert Bauer, Unterhaching (DE); Mina Hany Hanna Sedra, Munich (DE)

(73) Assignee: PIUR IMAGING GMBH, Vienna (AT)

( * ) Notice: Subject to any disclaimer, the term of this patent is extended or adjusted under 35 U.S.C. 154(b) by 166 days.

(21) Appl. No.: 17/910,554

(22) PCT Filed: Mar. 9, 2021

(86) PCT No.: PCT/EP2021/055908
§ 371 (c)(1),
(2) Date: Sep. 9, 2022

(87) PCT Pub. No.: WO2021/180715
PCT Pub. Date: Sep. 16, 2021

(65) Prior Publication Data
US 2023/0135757 A1    May 4, 2023

(30) Foreign Application Priority Data

Mar. 10, 2020   (EP) ..................................... 20162140

(51) Int. Cl.
*A61B 8/08*    (2006.01)
*A61B 8/00*    (2006.01)

(52) U.S. Cl.
CPC ............ *A61B 8/085* (2013.01); *A61B 8/4245* (2013.01); *A61B 8/483* (2013.01)

(58) Field of Classification Search
CPC ....... A61B 8/085; A61B 8/4245; A61B 8/483; A61B 8/5223; A61B 8/5253
See application file for complete search history.

(56) References Cited

U.S. PATENT DOCUMENTS 9,092,691 B1 *    7/2015   Beaumont .............. G06V 10/25
2009/0018445 A1 *  1/2009   Schers ................... A61B 8/483
                                                        600/437

(Continued)

FOREIGN PATENT DOCUMENTS

EP          3522789 A1    8/2019
WO       2019048482 A1    3/2019

OTHER PUBLICATIONS

Ni, D., et al. "Volumetric ultrasound panorama based on 3D SIFT." In: International conference on medical image computing and computer-assisted intervention, Springer 2008, pp. 52-60.

(Continued)

*Primary Examiner* — Jonathan Cwern
(74) *Attorney, Agent, or Firm* — Meunier Carlin & Curfman LLC

(57) ABSTRACT

A method and an apparatus for generating a combined three-dimensional ultrasound image of a body portion are described. Therein, two ultrasound scans are preformed, using a relative tracking system, specifically an inertial tracking, and two partial volume images are generated therefrom. The first and second volumes have an overlapping volume containing a predetermined anatomical structure. Then, respective anatomical structure position data indicative of the position of the predetermined anatomical structure in the respective partial volume image are identified by image segmentation. Then, an initial spatial relationship between the first and second partial volume images is established, based on the identified first and second anatomical structure position data. Then a fine registration algorithm using the initial spatial relationship as an initial input is carried out; and the partial volume images are combined in the common volume using the fine-registered spatial relationship.

26 Claims, 3 Drawing Sheets

(56) References Cited

U.S. PATENT DOCUMENTS

2010/0305449 A1* 12/2010 Wegener ............ G01S 7/52034
600/459
2018/0268541 A1  9/2018 Kruecker et al.
2019/0142392 A1* 5/2019 Carolus ............... A61B 8/5253
600/437
2020/0196894 A1* 6/2020 Govari .................. A61B 5/318

OTHER PUBLICATIONS

Ronneberger et al. "U-Net: Convolutional Networks for Biomedical Imaging Segmentation" (arXiv: 1505.04597, 2015).
Kutarnia, J. and Pedersen, P. "A Markov random field approach to group-wise registration/mosaicing with 10 application to ultrasound." In: Medical image analysis 24.1 (2015), pp. 106-124.
Schulte Zu Berge, C. et al., "Ultrasound Decompression for Large Field-of-View Reconstructions", in: Eurographics Workshop on Visual Computing in Biology and Medicine 2018, Granada, Spain, Sep. 2018.
International Search Report and Written Opinion filed in Application No. PCT/EP2021/055908, mailed Jun. 9, 2021, 16 pages.
Extended European Search Report filed in European Application No. 20162140.6, mailed Sep. 24, 2020, 9 pages.

* cited by examiner

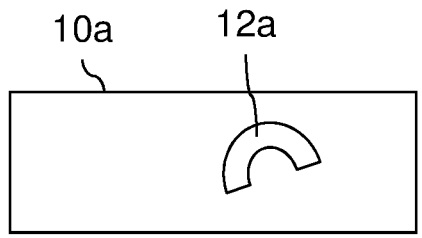
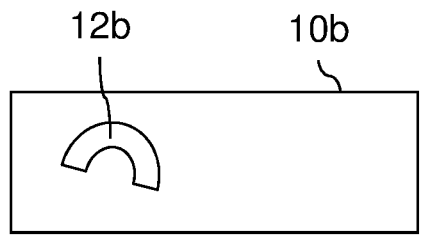
FIG. 2a   FIG. 2b
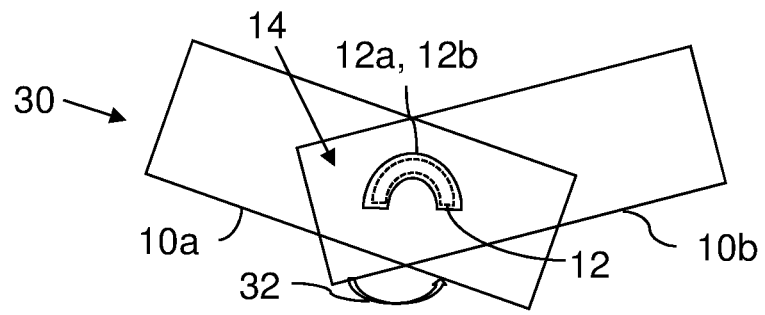
FIG. 2c
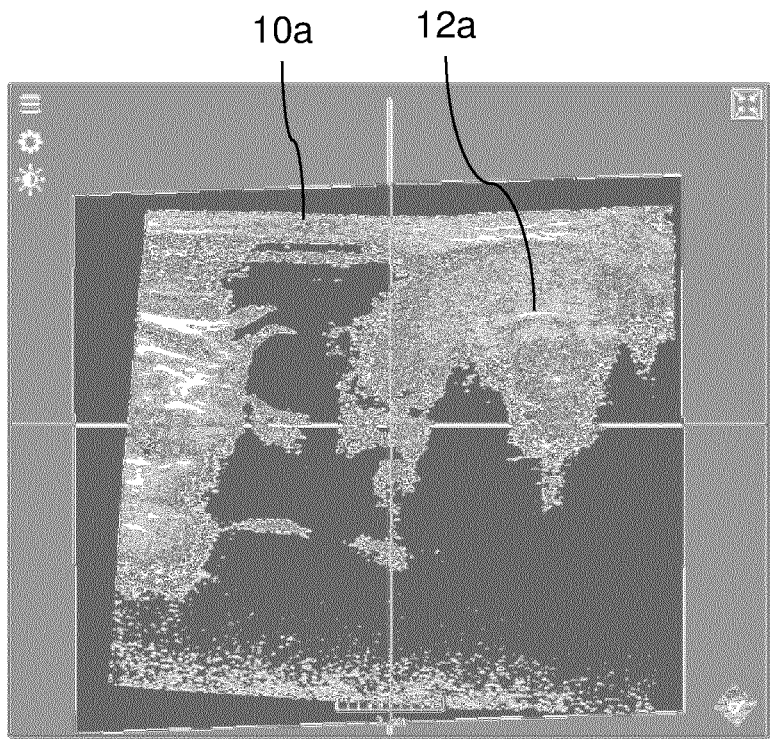
FIG. 3

METHOD AND APPARATUS FOR GENERATING A COMBINED THREE-DIMENSIONAL ULTRASOUND IMAGE

TECHNICAL FIELD

Embodiments of the present disclosure relate to the generation of a combined three-dimensional ultrasound image by combining (stitching) multiple partial volume images in a common volume. In particular, embodiments of the present disclosure relate to the combining of ultrasound images obtained with relative tracking, e.g. inertial tracking.

BACKGROUND

Ultrasound imaging has been extensively used as a medical imaging tool in the last several decades because of its safety, non-invasiveness and economical efficiency. Also, the acquisition and visualization of three-dimensional ultrasound images has become possible due to advances in digital storage and processing. However, full organs, bones and large fetuses can in many circumstances not be acquired in a single scan due to the limited field of view.

In order to solve this problem, several partial volume images, each obtained during a respective scan, are combined (stitched together). This combining requires the correct spatial relationship (spatial alignment in a common volume, i.e., in a common reference frame) of the partial volume images. This process that calculates the spatial relationship is also referred to as registration.

By obtaining the correct spatial relationship and combining (combination of the registered partial volume images, e.g., by image fusion) of multiple ultrasound partial volume images into a larger combined image, it becomes possible to not only enlarge the field of view of the resulting combined image. Further, also the quality of the combined image may be improved relative to the individual partial volume images, e.g., by correcting for occlusions (which can occur, e.g., due to bones and air as ultrasound can not penetrate them), reducing noise and other image artifacts, and by taking into account multiple scans of the same image portion from different viewing angles.

Obtaining these advantages requires a reliable registration of the three-dimensional partial volume images. One known registration method that has been used in the past is a rigid registration is using a tracking-based approach. Herein, the ultrasound probe is tracked with a (typically electromagnetic or optical) tracking system computing the absolute position of the ultrasound probe (e.g., 3 translational and 3 rotational coordinates), and thus allowing to compute the spatial relationship (transformation) between the partial volume images based on the tracked position. However, such systems add extra cost and complexity, such as the need for accurate calibration of the tracking system.

Another type of known registration method is imaged-based (feature-based) registration. This registration method uses image analysis of the partial volume images and relies on finding correspondences between two sets of features in pairs of partial volume images, and is exemplified by D. Ni, Y. Qu, X. Yang, Y. P. Chui, T.-T. Wong, S. S. Ho, and P. A. Heng. "Volumetric ultrasound panorama based on 3D SIFT." In: International conference on medical image computing and computer-assisted intervention, Springer 2008, pages 52-60. However, such methods are only able to handle small initial misalignments between 3D ultrasound volumes. The range of acceptable initial spatial relationship (possibly including a certain but not too large initial translational and rotational misalignment) is also referred to as the capture range of this method. Therefore, in the prior art, an approach has been used in which an initial registration is performed using an external absolute tracker, whereby the initial spatial relationship of the partial volume images is brought into the capture range, and subsequently imaged-based registration is performed for fine registration. Hence, also these approaches rely on an absolute tracking system and have the associated drawbacks.

SUMMARY

An object of the invention is to obtain a reliable combining of partial volume images, which avoids or alleviates at least some of the drawbacks discussed above.

In view of the above, a method according to claim 1 and an apparatus according to claim 13 are provided. Further details are provided in the dependent claims, the description herein, and in the drawings.

According to an aspect, a method and/or an apparatus for generating a combined three-dimensional ultrasound image of a body portion is provided. Therein, two ultrasound scans are preformed, using a relative tracking system, and two partial volume images are generated therefrom. The relative tracking system is an inertial tracking (comprising and) using an accelerometer and/or a gyroscope. The first and second volumes have an overlapping volume containing a predetermined anatomical structure. Then, respective anatomical structure position data indicative of the position of the predetermined anatomical structure in the respective partial volume image are identified by image segmentation. Then, an initial spatial relationship between the first and second partial volume images is established, based on the identified first and second anatomical structure position data (in particular, based on the data from the inertial tracking, and specifically from the accelerometer and/or gyroscope). Then a fine registration algorithm using the initial spatial relationship as an initial input is carried out; and the partial volume images are combined in the common volume using the fine-registered spatial relationship.

In particular, embodiments of the invention allow for a reliable yet simple and user-friendly combining of partial volume images. This advantage is obtained by having a robust yet simple and user-friendly initial registration step (establishing of an initial spatial relationship between the partial volume images), which thus does not necessarily rely on previous knowledge about the spatial relationship between the partial volume images and in particular does not necessitate the partial volume images to be in capture range. Thus, the initial registration step does not require any external reference to determine the spatial position, and in particular does not require any absolute tracking systems, and may even be tolerant regarding body movements in between ultrasound scans.

BRIEF DESCRIPTION OF THE DRAWINGS

So that the manner in which the above recited features of the present disclosure can be understood in detail, a more particular description of the disclosure, briefly summarized above, may be had by reference to embodiments. The accompanying drawings relate to embodiments of the disclosure and are described in the following:

FIG. 2a,b show schematically a respective first and second partial volume image generated by the method of FIG. 1;

FIG. 2c shows schematically the first and second partial volume images of FIGS. 2a, b arranged according to their established initial spatial relationship according to the method of FIG. 1;

FIG. 3 shows an example of a partial volume image generated according to an embodiment of the invention.

DETAILED DESCRIPTION OF ASPECTS AND EMBODIMENTS

Figure 1:
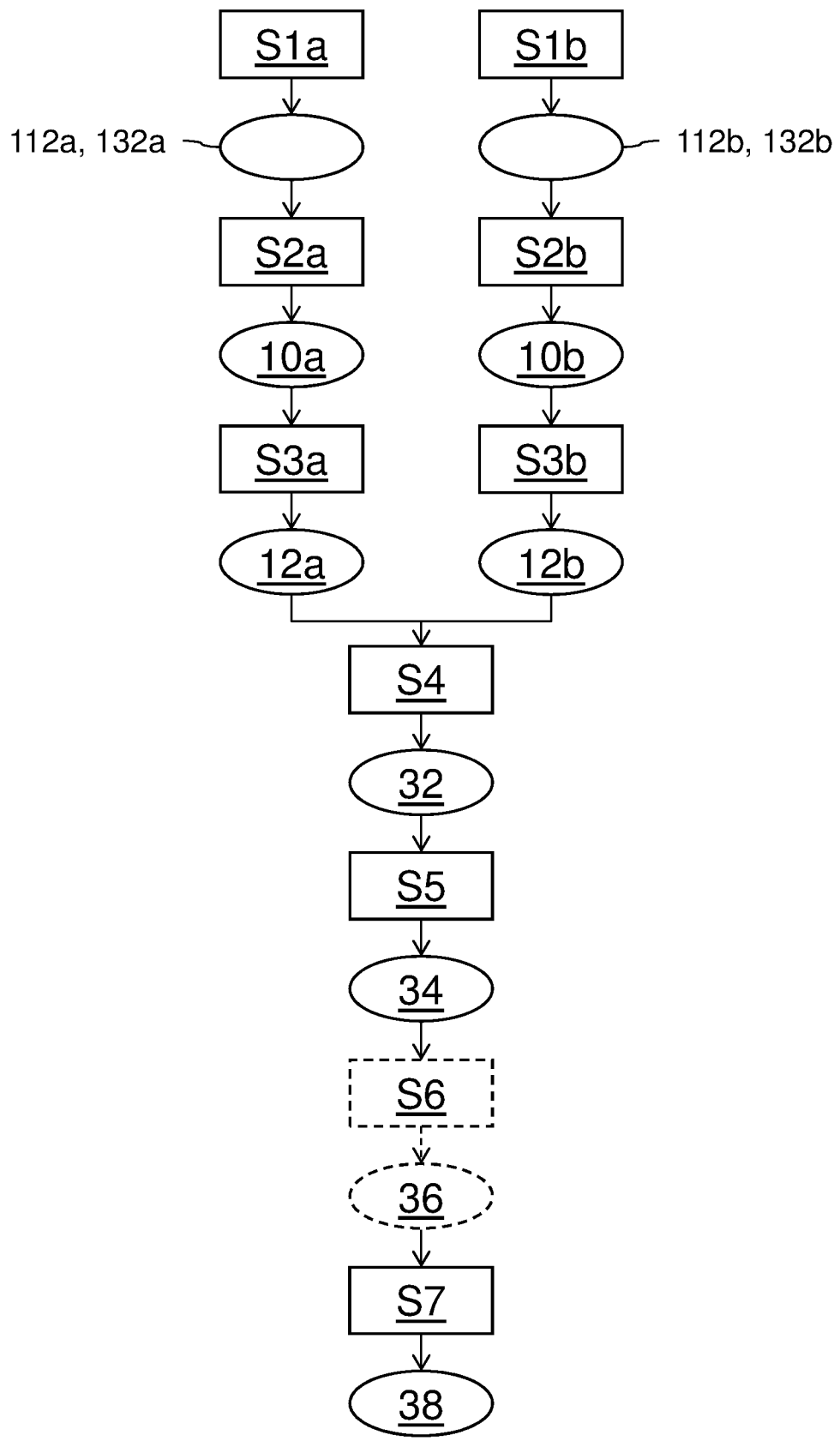
FIG. 1 shows a schematic flow diagram of a method according to an embodiment of the invention.

Reference will now be made in detail to the various embodiments, one or more examples of which are illustrated in each figure. Each example is provided by way of explanation and is not meant as a limitation. For example, features illustrated or described as part of one embodiment can be used on or in conjunction with any other embodiment to yield yet a further embodiment. It is intended that the present disclosure includes such modifications and variations.
Description of Overall Method First, with reference to FIG. 1, an embodiment of the method of the invention is described. The method generates a combined three-dimensional ultrasound image of a body portion and comprises the following steps shown in FIG. 1:

Step S1a is the step of performing a first ultrasound scan of a first volume of the body portion 102 using an ultrasound probe. In this step, the ultrasound probe generates first ultrasound image data 112a, and a relative tracking system 130 generates first relative displacement data 132a (e.g., indicating the relative displacement between the ultrasound images) by monitoring the relative displacement of the ultrasound probe 110.

The resulting first ultrasound image data 112a and first relative displacement data 132a are then taken as an input for the subsequent step S2a. In step S2a a first partial volume image 10a is generated from the first ultrasound image data 112a and from the first relative displacement data 132a.

After step S1a, another ultrasound scan is taken: Step S1b, analogous to step S1a, is the step of performing a second ultrasound scan of a second volume of the body portion 102 using the (same) ultrasound probe 110, whereby the ultrasound probe 110 generates second ultrasound image data 112b, and whereby the relative tracking system 130 generates second relative displacement data 132b by monitoring the relative displacement of the ultrasound probe 110. Then, step S2b, analogous to step S2a, is the step of generating a second partial volume image 10b from the second ultrasound image data 112b and from the second relative displacement data 132b.

The first and second volumes 10a, 10b have an overlapping volume 14, and this overlapping volume 14 contains a predetermined anatomical structure 12 of the body portion. Thus, according to an aspect, the method assumes previous knowledge about the anatomical structure 12, and imposes a protocol on the ultrasound image acquisition requiring that this anatomical structure 12 is included in both ultrasound scans.

Step S3a is the step of identifying first anatomical structure position data 12a indicative of the position of the predetermined anatomical structure 12 in the first partial volume image 10a, especially by image segmentation (of the first partial volume image 10a, which includes segmentation of underlying data such as the first ultrasound image data).

Analogously, step S3b is the step of identifying second anatomical structure position data 12b indicative of the position of the predetermined anatomical structure 12 in the second partial volume image 10b by image segmentation (of the second partial volume image 10b).

Step S4 is the step of establishing an initial spatial relationship 32 between the first and second partial volume images 10a, 10b obtained in steps S2a and S2b in a common volume 30. This initial spatial relationship 32 is established (calculated) based on the identified first and second anatomical structure position data 12a, 12b.

Step S5 is the step of adjusting the spatial relationship by a fine registration algorithm using the initial spatial relationship 32 as an initial guess; and Next, there is an optional step S6 of applying S6 an ultrasound decompression algorithm to the fine-registered spatial relationship 34.

Finally, step S7 is the step of combining the first and second partial volume images 10a, 10b in the common volume 30 using the adjusted spatial relationship 34, 36. An output of this step S7 may be a combined volume image based on the combination of the first and second partial volume images 10a, 10b. Here, the common volume 30 may be defined by a common reference frame such as a common coordinate system.

The method may in particular be applied for scanning of the thyroid gland. In this example, steps S1a and S2b can for example include the first and second ultrasound scans as left and right scan of a thyroid gland portion. The two scans are taken as left and right scans along a neck portion, each scan including a respective portion of the thyroid, and each scan including the trachea. Here, the trachea or a trachea portion such as the top arch portion may be used as the predetermined anatomical structure.

Next, further details and aspects of the method and of individual method steps and, correspondingly, to the corresponding parts and functions of the apparatus are described in more detail. These aspects may be used in any embodiment described herein such as in the method of FIG. 1 and/or in the embodiments shown in the other Figures, and reference signs relating to these Figures are included for illustration. But, the aspects are intended to be a general description of preferred optional aspects that may be used also independently of any embodiment, with or without being combined with other aspects.
Details and Aspects Relating to the Ultrasound Scans (Steps S1a, S2a):

In step S1a, a first ultrasound scan of a first volume of the body portion 102 using an ultrasound probe 110 is performed, whereby the ultrasound probe 110 generates first ultrasound image data 112a. The first ultrasound image data 112a may for example be a stream of ultrasound frames, such as (e.g., two-dimensional) ultrasound images taken in respective image plane or image regions (e.g. image cone) relative to the ultrasound probe.

The first ultrasound scan may be performed according to a scan protocol imposed on the user. The first ultrasound scan may be performed by moving the ultrasound probe along a skin surface of the body in a known manner.

The above description may apply analogously also to the second ultrasound scan in step S1b.

In an example of the first and second ultrasound scans, the ultrasound probe 110 is moved along a skin surface of the body portion. The motion of the probe is from a starting position to a final position of motion and may be imposed by a protocol. During the motion, the probe 110 collects ultrasound image data representing consecutive ultrasound image frames. Each ultrasound image frame provides an ultrasound image (i.e., graphically representable information of the ultrasound reflectivity properties) in a particular imaging region or image plane, i.e., in a two- or three-dimensional subspace of the volume portion. The imaging region has a predetermined shape and location relative to the ultrasound probe 110, and the imaging region moves jointly with the ultrasound probe 110. By moving the ultrasound probe 110, the image region is moved across the body portion so that the ultrasound image frames provide ultrasound images of the body portion.

Here, an ultrasound image frame is defined as a two- or three-dimensional ultrasound image taken at a given time using the ultrasound probe. The image frame represents an entire image of a pre-defined size as acquired by the ultrasound probe. Subsequent image frames usually have the same resolution. In contrast, a dynamically selected subset of an ultrasound image frame, selected in dependence of the image content and possibly with variable size, is not an image frame. Typically, a time stamp is associated with the ultrasound image frame. The probe 110 collects the ultrasound image data as a data stream representing consecutive ultrasound image frames.

According to an aspect, the first and second volumes of the ultrasound scans S1a, S2a are substantially different from each other, so that the overlapping volume of the first and second volumes is less than 70 vol % (preferably less than 50 vol %, more preferably less than 30 vol %) of the first volume and/or of the second volume. Herein, the vol % may be measured by the volume of the respective image portions in the final combined image 38 obtained as an output of the method. According to an aspect, the overlapping volume contains the predetermined anatomical structure.

According to an aspect, the first and second ultrasound scans are performed during a single ultrasound scan procedure, e.g., immediately after each other, (without performing any intervention on the body in the meantime). In particular, according to an aspect, the relative tracking system remains activated during the single ultrasound scan procedure, and/or the same ultrasound probe is used for steps S1a and S1b.

According to an aspect, the body portion 102 includes the thyroid gland. In this case the predetermined anatomical structure 12 may be a trachea portion such as an arch portion (top arch portion) of the trachea.

According to a further aspect, the body portion 102 includes a blood vessel and preferably is a limb portion or a neck portion. In this case the predetermined anatomical structure 12 may be a bone portion or a muscle portion.

According to a further aspect, the method may comprise more than two ultrasound scans, for example a third and possibly a fourth ultrasound scan, or even more. For these additional ultrasound scans, the description of the second ultrasound scan applies analogously. All of the ultrasound scans may include a common anatomical structure, whereby the steps S4 and S5 are carried out for all ultrasound scans and resulting data. In a further aspect, pairs of ultrasound scans may include a pairwise anatomical structure, whereby the steps S4 and S5 are carried out pairwise.

Details and Aspects Relating to the Relative Tracking (Steps S1a, S1b):

In steps S1a, S1b, the relative tracking system generates relative displacement data 132a by monitoring the relative displacement of the ultrasound probe 110. The displacement may be indicative of the three-dimensional displacement from one ultrasound frame to the next of the stream. The displacement may thus also be indicative of the displacement of the ultrasound probe 110 relative to the body portion 102.

Here, the relative displacement may indicate a relative translation as well as a relative orientation change, and the relative displacement data may thus be parametrized by six parameters (three translational and three rotational degrees of freedom).

Here, "relative tracking system" refers to a system that only tracks incrementally the relative motion of the ultrasound probe, e.g., in between frames and/or during time intervals, but does not use any external reference to determine the spatial position, and in particular does not track absolute positions (i.e., positions relative to an "absolute" reference frame available at all times of the tracking, e.g., relative to a—typically stationary—reference object of the tracking system defining the reference frame). For a relative tracking system, at least approximate absolute positions may still be obtained by integration of the incrementally tracked motion.

An example of a relative tracking system is an inertial tracking using, e.g., an accelerometer and/or a gyroscope (an inertial tracking system comprising the accelerometer and/or gyroscope), possibly in an integrated IMU. The inertial tracking may for example continuously monitor the acceleration and/or gyroscopic data obtained by the accelerometer and/or a gyroscope, and integrate this acceleration and/or gyroscopic data for obtaining the relative positional change of the ultrasound probe. The inertial tracking may be adapted for monitoring the six degrees of freedom of the relative motion of the ultrasound probe.

An advantage of such an inertial tracking system is the fact that it provides a reliable information about the relative motion of the ultrasound probe in a manner that is independent from the ultrasound images. The relative tracking information from the inertial tracking system therefore complements the information from the ultrasound images, because the inertial tracking is strong in areas in which other tracking methods are weaker, and vice versa. Examples for such areas are, e.g., accurately estimating rotational movement and/or dealing with symmetries and resulting ambiguities in an image-based approach regarding the direction taken by the ultrasound probe, for example. Optionally, the information from the inertial tracking system can be combined with and/or compared to relative tracking information based on ultrasound data, for further increasing and/or validating the reliability of the relative tracking information.

An advantage of such an inertial tracking system is the fact that it may be independent from any external reference, thereby increasing versatility and reliability in a large number of circumstances.

Especially in case of the inertial tracking system comprising a gyroscope, the relative tracking of the rotational degrees of freedom is particularly accurate using inertial tracking for the relative tracking.

Furthermore, an inertial tracking system can be integrated with the ultrasound probe in an easy and cost-efficient manner. It is even possible to retrofit existing ultrasound probes using the inertial tracking system.

The inertial tracking system may be rigidly attached to the ultrasound probe. The inertial tracking system may be integrated with the ultrasound probe and be provided in the housing of the ultrasound probe. Alternatively, the inertial tracking system may be fixedly attached to the ultrasound probe in a removable manner, preferably attached to a defined inertial tracking system receiving section of the ultrasound probe, whereby the inertial tracking system is in a defined position relative to the ultrasound probe when attached to the ultrasound probe. According to an aspect, the displacement of the ultrasound probe 110 is monitored by the relative tracking system 130 only (specifically, by the inertial tracking system only), without an absolute position of the ultrasound probe 110 being tracked.

According to an aspect, the relative displacement data, indicative of the three-dimensional motion, has six degrees of freedom and includes a translation (three degrees of freedom) and a rotation (three degrees of freedom) from frame to frame. The relative displacement data may include any parametrization of these degrees of freedom, or at least of a subset of these degrees of freedom. According to an aspect, the ultrasound probe is a free-hand probe and has the full six degrees of freedom. According to another aspect, the ultrasound probe is subject to constraints limiting the degrees of freedom to less than six.

According to an aspect, the relative tracking system 130 includes at least one of an IMU sensor, an acceleration sensor, a gyroscopic sensor, and a machine learning module having been trained to determine the relative three-dimensional motion between ultrasound image frames.

The relative displacement data may, in particular, be obtained by any method disclosed in WO 2019/048482 A1, whose content is included in its entirety by reference. Thus, according to an aspect, the relative tracking system generates relative displacement data 132*a* by a method of determining a three-dimensional motion of the movable ultrasound probe, the method comprising:

Receiving a stream of ultrasound image data (the first/second ultrasound image data 112*a*) from the ultrasound probe while the ultrasound probe is moved along the volume portion (body portion);

Inputting at least a sub-set of the ultrasound image data representing a plurality of ultrasound image frames into a machine-learning module, wherein the machine learning module has been trained to determine the relative three-dimensional motion between ultrasound image frames; and Determining, by the machine-learning module, a three-dimensional motion indicator indicating the relative three-dimensional motion between the ultrasound image frames.

The machine learning module may comprise a neural network, preferably a convolutional neural network. The step of inputting the at least sub-set of the ultrasound image data may include inputting local image data corresponding to a pair of ultrasound image frames to the machine learning module, and the three-dimensional motion indicator may indicate the relative three-dimensional motion between the pair of ultrasound image frames. The inputting and determining steps may be repeated for consecutive pairs or subsets of image frames.

According to an aspect, the relative tracking system 130 is adapted for determining only relative motion between image frames of the first and second ultrasound image data, but no absolute motion. In other words, absolute position in a reference frame can only be obtained by integration of the relative motion but not in a more direct manner.

Details and Aspects Relating to the Generating of Partial Volume Images (Steps S2*a*, S2*b*):

Steps S2*a* and S2*b*, include, according to an aspect, the reconstruction of a three-dimensional ultrasound image (partial volume image) using the respective relative displacement data (e.g., the relative probe positions and orientations) and the stream of ultrasound image data.

This step is generally known in the art, and may be carried out by any known 3D ultrasound volume compounding and/or reconstruction algorithm. An example for such an algorithm is described in the textbook "3D Freehand Ultrasound: Reconstruction and Spatial Compounding" by R. N. Rohling (1999).

Details and Aspects Relating to the Segmentation (Steps S3*a*, S3*b*):

Steps S3*a* and S3*b* include the identification of respective anatomical structure position data 12*a*, 12*b* indicative of the position of the predetermined anatomical structure 12 in the respective partial volume image 10*a*, 10*b*. The identification is, in particular, carried out by image segmentation. Thus, the partial volume images obtained from these scans are passed to a segmentation model to identify (label) the predetermined anatomical structure 12.

Herein, segmentation of the respective partial volume image may include classifying the voxels as one of multiple classes, either by probability maps or (e.g., after a thresholding and/or maximum value selection) by a class label for each voxel. For instance, the class may include one class for belonging to the predetermined anatomical structure and one or multiple classes for not belonging to the predetermined anatomical structure. Then, a class label may for example be a binary label indicating whether or not a voxel belongs to the predetermined anatomical structure. In a more complex setting, the label may have additional entries, e.g., to segment at least some of the skin, the fat, the muscle and the bone voxels. Here, the voxels referred to for segmentation may correspond to the image voxels, but may also be different, e.g., coarser voxels.

The segmentation may be carried out using the three-dimensional image as an input. This also includes the case of using a constituting stream of two-dimensional images as an input, and performing two-dimensional segmentation on each of the two-dimensional images, thereby obtaining two-dimensional classification (e.g., labels, probability maps) for each of the two-dimensional images. In this case, the above description of voxels includes the two-dimensional pixels of each of the images. Then, this classification may be compounded to a three-dimensional classification in the analogous manner in which the two-dimensional images are compounded.

Thus, the segmentation step may be carried out by segmenting each two-dimensional image, then combining the labeled image to a respective three-dimensional volume image, or by directly segmenting the three-dimensional volume images. The resulting labeled volume images indicate the position of the predetermined anatomical structure in the respective partial volume image.

According to an aspect, the labeled (2D or 3D) images for the first and the second volume may be further processed. For example, the background of the labeled (2D or 3D) images for the first and the second volume may be cropped via thresholding. The labels may pass by further pre-processing blocks where for further image processing methods, e.g., by cutting out background (non-anatomical structure) voxels leaving only the anatomical structure in 3D as shown in FIGS. 2*a*, 2*b*, and 3.

The labeled image may include a segmentation label indicating whether the respective image portion belongs to the anatomical structure (e.g., binary or continuous likelihood information).

According to an aspect, and irrespective of the details of the segmentation algorithm, the segmentation algorithm may output a three-dimensional classification output (e.g., a map of classification labels and/or probabilities as function of position in the partial volume image). Thus, the output of segmenting the anatomical structure may be a labeled volume image for the first volume image and a labeled volume image of the second volume image.

The three-dimensional classification output is indicative of the position of the predetermined anatomical structure 12 in the respective partial volume image 10a, 10b, and is therefore an example of anatomical structure position data 12a, 12b. Here, "position" may be expressed by three coordinates indicating the position of a representative point of the predetermined anatomical structure, such as the center of mass, and may optionally further include additional parameters such as the orientation and/or the size of the predetermined anatomical structure, for example as extracted from the label map. Alternatively, the anatomical structure position data may be represented by the full label map.

According to an aspect, a deep learning algorithm, for example using a convolutional neural network (CNN), may be used for segmentation. Such algorithms are generally known and have been described, for example, in Long et al. (2015); Badrinarayanan et al. (2015).

According to a particular aspect, a U-Net Convolutional Networks is used as described in Ronneberger et al., "U-Net: Convolutional Networks for Biomedical Image Segmentation" (arXiv:1505.04597, 2015).

According to an aspect, the first and second partial volume images (10a, 10b) are segmented using a convolutional neural network such as a 2D u-net, applied to the stream of image frames from which the respective partial volume images are compounded.

Next, the training of the U-Net Convolutional Networks used in this example is described. The input for training the UNet is ultrasound images (two-dimensional images of a trachea, corresponding to the image frames) with their corresponding label maps, e.g., binary label maps indicating whether the portion belongs to the anatomical structure (top arc portion of the trachea) or not. With this training data, the model is trained via stochastic gradient descent, as described in Ronneberger et al. (cited above). The trained model can then be used to extract label maps from the acquired ultrasound image frames.

According to an aspect, the trachea or a trachea portion such as the top arch portion is used as the predetermined anatomical structure.

The use of the trachea or a trachea portion has the advantage that it is present in each thyroid scan and that it can be discerned reliably in ultrasound images due to its unique appearance. In particular, the presence of the air within the trachea gives it a high contrast in the ultrasound scans.

Further, using an arc portion of the trachea has the advantage of removing or reducing rotational ambiguities due to the (imperfect) cylindrical shape of the trachea, and thus of assuring that in the registration step the correct rotation can be found.

FIG. 2a, 2b show schematic examples of an output from the segmentation steps S3a and S3b, respectively. In FIG. 2a, the first partial volume image 10a is shown, and the three-dimensional classification output is shown as a map of classification labels. Here, region 12a is the region with labels for the predetermined anatomical structure. The map of classification labels, as illustrated by the region 12a, is indicative of the position of the predetermined anatomical structure and is therefore the first anatomical structure position data 12.

Likewise, FIG. 2b shows the second partial volume image 10b and the region 12b thereof having labels for the predetermined anatomical structure.

FIG. 3 shows an image of a two-dimensional image frame belonging to a partial volume image 10a, and the region 12a with labels for the predetermined anatomical structure (top arc of the trachea), thus corresponding to the situation schematically shown in FIG. 2a.

Details and Aspects Relating to the Establishing of an Initial Spatial Relationship (Step S4)

Next, aspects relating to the step S4 of establishing an initial spatial relationship is described. The establishing an initial spatial relationship may also be referred to as image registration of the first and second partial volume images 10a, 20a. Herein, image registration is understood as the process of transforming different sets of data into one coordinate system.

Thus, in step S4, the initial spatial relationship between the first and second partial volume images is calculated using the position information 12a, 12b from the classification step S3, e.g., the labeled volume images. This initial spatial relationship may be a transformation matrix.

An example of using the position information for calculating the transformation matrix may is as follows: Using the labeled volume images of the predetermined anatomical structure, its center of mass and orientation is calculated in each of the partial volume images, and the transformation is selected such that the center of mass and orientation are aligned in the common volume.

The establishing of an initial spatial relationship is different from fine registration. Fine registration does not establish an initial spatial relationship but receives, as an input, already an approximate spatial relationship which should be within the capture range of the fine registration. In contrast, the establishing of an initial spatial relationship does not receive such an input, and thus merits the term "initial".

For example, an initial input (guess) used for the establishing of an initial spatial relationship by an iterative method may be obtained may be just a random initial guess. The initial input also may be non-random and may for example be obtained from the input data used for determining the initial spatial relationship, e.g., from a rough image analysis of the first and second partial volume images and/or from relative tracking data. The input data (initial guess) is, however, not based on data from an absolute tracking system.

Thus, according to an aspect, the initial spatial relationship is obtained without any input from an absolute tracking system.

Referring to FIG. 2c as an example illustration, the initial spatial relationship 32 is, according to an aspect, a three-dimensional relationship between the first and second partial volume images 10a, 20a in a common volume 30. The spatial relationship 32 can be expressed by a transformation function (e.g., matrix) transforming the coordinate systems of the first and second partial volume images 10a, 20a to each other and/or to the coordinate system of the common volume. The initial spatial relationship 32 between the first and second partial volume images 10a, 20a may include a translational relationship and/or a rotational relationship.

According to an aspect, the spatial relationship may for example be a spatial relationship in three-dimensional space. The spatial relationship (transformation function) can for example be a rigid transformation having six degrees of freedom (three rotational and three translational degrees of freedom), but it may also have less degrees of freedom, e.g., by taking into account boundary conditions, or more degrees of freedom, e.g., by allowing for additional non-rigid transformations.

According to an aspect, the initial spatial relationship between the first and second partial volume images is established by a position aligning algorithm, the position aligning algorithm being configured for aligning the position of the predetermined anatomical structure 12 in the first partial volume image 10a and the position of the predetermined anatomical structure 12 in the second partial volume image 10b with each other, and/or with a position of the predetermined anatomical structure 12 in the common volume 30.

According to an aspect, the position aligning algorithm may be configured for minimizing a spatial misalignment functional as a function of the spatial relationship between the first and second partial volume images, wherein the spatial misalignment functional further depends on the first and second anatomical structure position data 12a, 12b.

According to an aspect, the spatial relationship is determined based on the identified first and second anatomical structure position data 12a, 12b. According to an aspect, the first and second anatomical structure position data 12a, 12b are label maps, and the spatial relationship is obtained by aligning the label maps to each other (registration of the label maps), possibly via a predetermined label map of the predetermined anatomical structure.

According to an aspect, each of the first and second anatomical structure position data 12a, 12b include the center of the mass of the anatomical structure as determined in each of the volume images by the classification (e.g., center of the mass of the respective label maps). Then, the translation between the first and second partial volume images 10a, 20a is calculated by aligning the centers of mass with each other.

Likewise, according to an aspect, each of the first and second anatomical structure position data 12a, 12b include an orientation indicator of the anatomical structure as determined in each of the volume images by the classification (e.g., three-dimensional angular information, such as a vector, indicating the orientation of the respective label maps). Then, a rotation between the first and second partial volume images 10a, 20a is calculated by aligning the orientation indicators with each other.

But the orientation may also be determined in an alternative or additional manner, for example using a gyroscope. According to an aspect, the relative tracking system includes a gyroscopic sensor, and wherein the initial spatial relationship between the first and second partial volume images is established by using an integrated gyroscopic signal of the gyroscopic sensor as a further input. The (additional) use of an gyroscope input may be advantageous, especially if the predetermined anatomical structure has an approximate rotational symmetry.

According to an aspect, the translational but not the rotational relationship is obtained based on the first and second anatomical structure position data 12a, 12b. This aspect has the advantage that the translation of an inertial tracking has a relatively poor reliability, whereas, e.g., a gyroscope has a high reliability for tracking rotation. Thus, the rotational relationship may be obtained with sufficient reliability using the integrated gyroscope, whereas the translational relationship is obtained according to step S4 as described herein, based on the first and second anatomical structure position data 12a, 12b.

According to an aspect, it is provided an initial registration module 144 adapted for establishing an initial spatial relationship 32 between the first and second partial volume images 10a, 10b based on the identified anatomical structure 12 in the first and second partial volume images 10a, 10b. For example, it is described according to embodiments herein to establish a translational relationship of the initial spatial relationship 32 based on labeled images of the anatomical structure 12 in the first and second partial volume images 10a, 10b. In particular, the translational relationship (between the first and second partial volume images 10a, 10b) may be established based on the anatomical structure 12 in the first and second partial volume images 10a, 10b as identified by image segmentation.

According to the same aspect, it is provided a relative tracking system 130 that is fixable to the ultrasound probe 110, and adapted for generating relative displacement data by monitoring the relative displacement of the ultrasound probe, wherein the relative tracking system 130 is an inertial tracking using an accelerometer and/or a gyroscope. For example, it is described according to embodiments herein to establish a rotational relationship of the initial spatial relationship 32 based on an integrated gyroscopic signal. In particular, the rotational relationship (between the first and second partial volume images 10a, 10b) may be established based on data obtained from the gyroscope at least in a time period between the first and second ultrasound scans, potentially further including time periods of the first and second ultrasound scans.

According to the same aspect, it is provided a combining module 147 adapted for combining the first and second partial volume images 10a, 10b based at least on the initial spatial relationship 32 as described herein.

Beneficially, a lightweight yet effective method and apparatus for combining three-dimensional ultrasound images of an anatomical structure is provided by the aspect described above and embodiments described herein, and the challenge of difficult combinations, in particular, of anatomical structures having some degree of rotational or translational symmetry, can be addressed simply, e.g. without complex absolute tracking systems.

For example, where the anatomical structure has high rotational symmetry (but where translational symmetry is not particularly high), further input from the relative tracking system using inertial tracking, e.g. rotational relationship/integrated gyroscopic signal (such as data obtained in the time between scans), in addition to the information in the ultrasound scans, e.g. anatomical structure position data (e.g. based on image segmentation), helps to break the rotational symmetry, without resorting to absolute tracking systems which require calibration etc.

Vice versa, it can be understood that where the anatomical structure has high translational symmetry (but where rotational symmetry is not particularly high), further input from the relative tracking system using inertial tracking, e.g. translational relationship/integrated accelerometer signal (such as data obtained in the time between scans), helps to break the translational symmetry. In the case where both rotational and translational symmetry is particularly high, the relative tracking system using inertial tracking may combine data from both an accelerometer and gyroscope.

Additionally, relative tracking system using inertial tracking is particularly suited because the drift errors associated with inertial tracking is not particularly detrimental over the short periods between consecutive ultrasound scans, particularly as described in embodiments herein, thus the provision of relative tracking system as a relatively lightweight further input to address rotational/translational symmetry is particularly efficient.

Accordingly, a lightweight yet effective method and apparatus for combining three-dimensional ultrasound images of an anatomical structure is provided by aspects and embodiments described herein.

According to an alternative or additional aspect, the first and second anatomical structure position data 12a, 12b include a respective first and second label map (classification label/probability map), and the determining of the spatial relationship includes finding a transformation function by minimizing a deviation of the first and second label map (which includes the cases of minimizing a deviation between the first and the second label map; and/or minimizing a deviation between the first label map and a predetermined label map of the anatomical structure in the common volume, and minimizing a spatial misalignment functional between the second label map and a predetermined label map of the anatomical structure in the common volume).

The spatial misalignment functional may express the spatial overlap of the predetermined anatomical structure 12 in the first and second partial volume image 10a, 10b as a function of the first and second anatomical structure position data 12a, 12b and of the spatial relationship between the first and second partial volume images. Then, the initial spatial relationship is obtained by minimizing the spatial misalignment functional, possibly subject to further boundary conditions or punishing functions. For example, the first and second anatomical structure position data 12a, 12b may be first and second labeled images of the anatomical structure 12, and the spatial misalignment functional may express the spatial overlap of the first and second labeled images as a function of the spatial relationship between the first and second partial volume images.

According to a further aspect, the spatial relationship is determined by minimizing a spatial misalignment functional as a function of the position of the first partial volume image in the common volume, wherein the spatial misalignment functional depends on the first anatomical structure position data 12a and expresses a misalignment with a position of the predetermined anatomical structure 12 in the common volume 30, thereby identifying a position of the first partial volume image in the common volume; and minimizing a spatial misalignment functional as a function of the position of the second partial volume image in the common volume, wherein the spatial misalignment functional depends on the second anatomical structure position data 12b and expresses a misalignment with a position of the predetermined anatomical structure 12 in the common volume 30, thereby identifying a position of the second partial volume image in the common volume]

Thus, the first and second anatomical structure position data 12a, 12b may be first and second labeled images of the anatomical structure 12 obtained during the segmentation step and indicating the belonging, or likelihood of belonging, to the anatomical structure. The initial spatial relationship 32 between the first and second partial volume images may be determined by bringing the anatomical structure to a maximum overlap with each other or with a predefined map of the anatomical structure in the common volume.

According to an aspect, the spatial relationship is determined by assigning a same position, in the common volume, for the identified positions of the predetermined anatomical structure in the first and second partial volumes.

According to an aspect, the initial spatial relationship (32) between the first and second partial volume images may be established (exclusively) based on the identified first and second anatomical structure position data (12a, 12b), and further optionally on relative displacement data generated by the relative tracking system 130 (e.g., the first, second relative displacement data and/or relative displacement data obtained in between the first and second ultrasound scan) and/or on assumptions regarding the motion protocol of the ultrasound probe.

Details and Aspects Relating to the Fine Registration Algorithm and Further Image Adaptations (Steps S5, S6)

In step S5, this initial spatial relationship (transformation matrix) is passed to image registration and used as initialization for (image-based) fine registration.

Generally, fine registration algorithms for adjusting a spatial relationship (step S5) are known. Here, a known fine registration algorithm is implemented, for example an algorithm as described in D. Ni et al (2008, cited in the technical background section of this specification); and/or in J. Kutarnia and P. Pedersen. "A Markov random field approach to group-wise registration/mosaicing with application to ultrasound." In: Medical image analysis 24.1 (2015), pages 106-124.

The fine registration algorithm uses the initial spatial relationship from step S4 as an initial guess, whereby the initial spatial relationship is, or is very likely to be, in a capture range of the fine registration algorithm.

According to an aspect, the fine registration algorithm includes optimizing an objective function. According to an aspect, the fine registration algorithm is a cross-correlation algorithm. The optimizing may include, for example, a bound optimization by quadratic approximation (BOBYQA) optimizer and/or a normalized cross correlation (NCC) similarity metric.

According to an aspect, the method further comprises a step S6 of applying an ultrasound decompression algorithm to the fine-registered spatial relationship. A fine registration followed by such a decompression algorithm is described in C. Schulte zu Berge, M. Salehi, F. Bender, W. Wein, "Ultrasound Decompression for Large Field-of-View Reconstructions", in: Eurographics Workshop on Visual Computing in Biology and Medicine 2018, Granada, Spain, September 2018.

Details and Aspects Relating to the Combining in the Common Volume (Step S7)

The combination of the first and second partial volume images in the common volume 30 using the determined (adjusted) spatial relationship is known in the art, and is generally also referred to as stitching. Here, according to an aspect, the combining is a monomodal combining of ultrasound images, using the spatial relationship obtained by monomodal 3D registration. The step of combining the (fine-registered) images in the common volume is described, for example, in references cited in the previous section (Details and aspects relating to the steps S5, S6).

Apparatus

Figure 4:
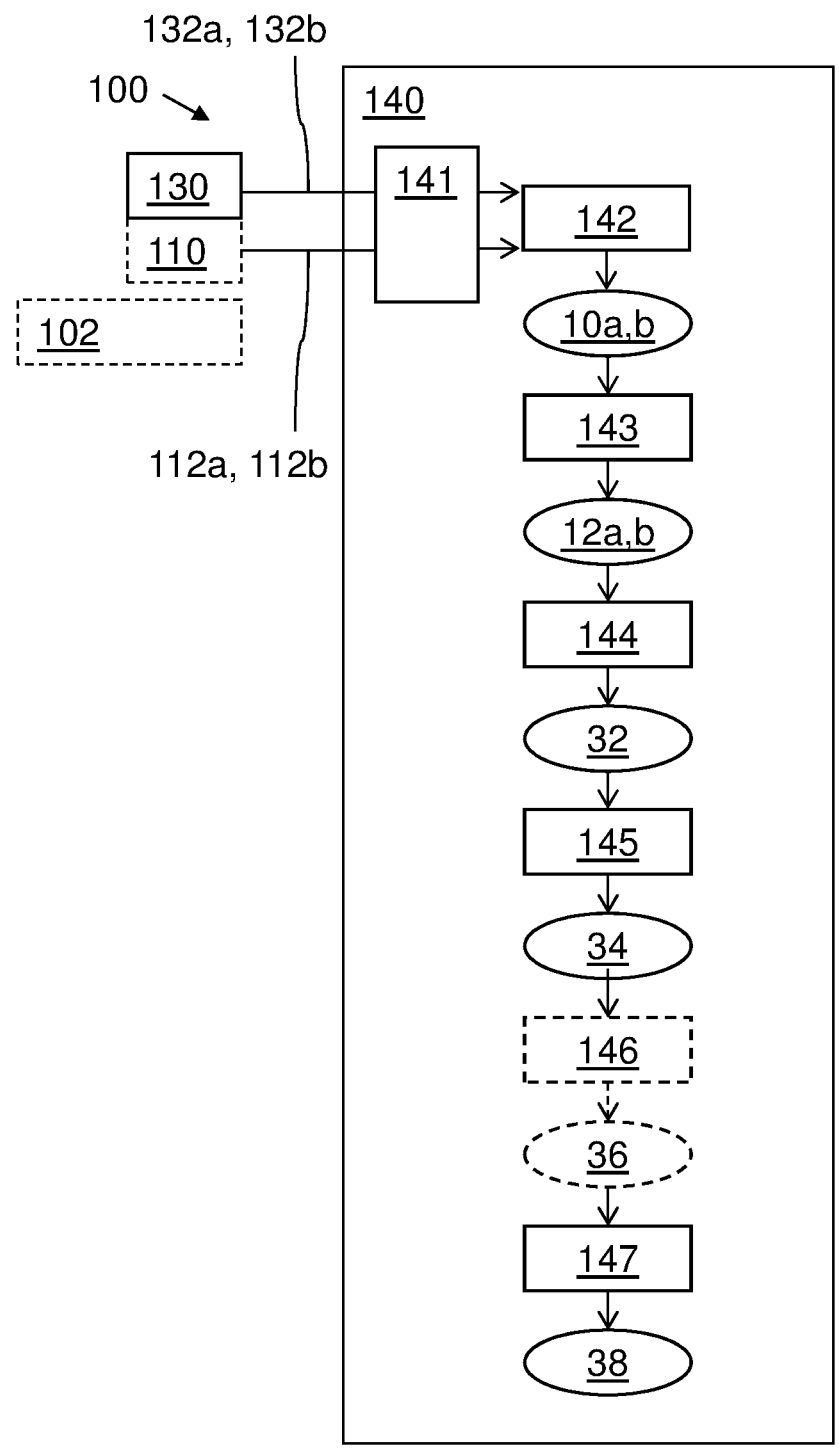
FIG. 4 shows a schematic diagram of an apparatus according to an embodiment of the invention.

Embodiments of the invention also include an apparatus configured for carrying out the method described herein. Such an apparatus is shown schematically in FIG. 4. The apparatus 100 of FIG. 4 is an apparatus for generating a combined three-dimensional ultrasound image of a body portion 102. The apparatus 100 comprises a relative tracking system 130 and an ultrasound image combining system 140.

The relative tracking system 130 is fixable to an ultrasound probe 110 and is adapted for generating relative displacement data by monitoring the relative displacement of the ultrasound probe 110.

The ultrasound image combining system 140 comprises the following:

an input interface 141 adapted for receiving first and second ultrasound image data 112a, 112b generated by the ultrasound probe 110 during a first and second ultrasound image acquisition, respectively, and first and second relative displacement data 132*a*, 132*b* generated by the relative tracking module 130 during the first and second ultrasound image acquisition, respectively;

an image reconstruction module 142 adapted for reconstructing a first and second partial volume image 10*a*, 10*b* from the received first and second ultrasound image data and from the received first and second relative displacement data, respectively;

an image segmentation module 143 adapted for identifying first anatomical structure position data 12*a* indicative of the position of the predetermined anatomical structure 12 in the first partial volume image 10*a* and for identifying second anatomical structure position data 12*b* indicative of the position of the predetermined anatomical structure 12 in the second partial volume image 10*b* by image segmentation of the first and second partial volume image 10*a*, 10*b*, respectively;

an initial registration module 144 adapted for establishing an initial spatial relationship 32 between the first and second partial volume images 10*a*, 10*b* in a common volume 30, based on the identified predetermined anatomical structure 12*a*, 12*b* in the first and second partial volume images 10*b*;

a fine registration module 145 adapted for adjusting the spatial relationship by a fine registration algorithm using the initial spatial relationship 32 as an initial guess; and a combining module 147 adapted for combining the first and second partial volume images 10*a*, 10*b* in the common volume 30 using the adjusted spatial relationship 34, 36.

The apparatus is configured for carrying out the method described herein, and the details and aspects described herein for the method are applicable in a corresponding manner to the apparatus 100.

While the foregoing is directed to embodiments, other and further embodiments may be devised without departing from the basic scope, and the scope is determined by the claims that follow.

The invention claimed is:

1. A method for generating a combined three-dimensional ultrasound image of a body portion, the method comprising:
   performing a first ultrasound scan of a first volume of the body portion using an ultrasound probe, whereby the ultrasound probe generates first ultrasound image data, and whereby a relative tracking system generates first relative displacement data by monitoring the relative displacement of the ultrasound probe;
   generating a first partial volume image from the first ultrasound image data and from the first relative displacement data;
   performing a second ultrasound scan of a second volume of the body portion using the ultrasound probe, whereby the ultrasound probe generates second ultrasound image data, and whereby the relative tracking system generates second relative displacement data by monitoring the relative displacement of the ultrasound probe,
   generating a second partial volume image from the second ultrasound image data and from the second relative displacement data,
   wherein the first and second volumes have an overlapping volume containing a predetermined anatomical structure of the body portion;
   identifying first anatomical structure position data indicative of the position of the predetermined anatomical structure in the first partial volume image by image segmentation;
   identifying second anatomical structure position data indicative of the position of the predetermined anatomical structure in the second partial volume image by image segmentation; and
   establishing an initial spatial relationship between the first and second partial volume images in a common volume, based on the identified first and second anatomical structure position data;
   adjusting the spatial relationship by a fine registration algorithm using the initial spatial relationship as an initial guess; and
   combining the first and second partial volume images in the common volume using the adjusted spatial relationship,
   wherein the relative tracking system is an inertial tracking system using at least one from a group comprising an accelerometer and a gyroscope, and
   wherein segmentation of the first partial volume image and the second partial image volume comprises classifying voxels of the first partial volume image and the second partial image volume as one of multiple classes, either by probability maps or by a class label for each voxel, and outputs a three-dimensional classification output.

2. The method according to claim 1, wherein establishing the initial spatial relationship is based on data from at least one from the group comprising the accelerometer and the gyroscope, obtained at least in a time period between the first and second ultrasound scans.

3. The method according to claim 1, wherein establishing the initial spatial relationship is based on an integrated signal from at least one from the group comprising the accelerometer and the gyroscope.

4. The method according to claim 1, wherein establishing a rotational relationship of the initial spatial relationship is based on data from the gyroscope obtained at least in a time period between the first and second ultrasound scans.

5. The method according to claim 1, wherein establishing a rotational relationship of the initial spatial relationship is based on an integrated gyroscopic signal.

6. The method according to claim 1, wherein establishing the initial spatial relationship, which is a translational relationship, is based on the first and second anatomical structure position data.

7. The method according to claim 1, wherein establishing an initial rotational relationship between the first and second partial volume images is based on data obtained from the gyroscope at least in a time period between the first and second ultrasound scans.

8. The method according to claim 1, wherein the initial spatial relationship is obtained without any external reference to determine the spatial position and without any input from an absolute tracking system.

9. The method according to claim 1, wherein the relative tracking system remains activated between the first and second ultrasound scans.

10. The method according to claim 1, wherein the first and second volumes are different from each other, so that the overlapping volume of the first and second volumes is less than 70 vol % of the first volume and less than 70 vol % of the second volume.

11. The method according to claim 1, wherein the three-dimensional displacement of the ultrasound probe is monitored by the relative tracking system only, without an absolute position of the ultrasound probe being tracked.

12. The method according to claim 1, wherein the first and second ultrasound scans are performed during a single ultrasound scan procedure.

13. The method according to claim 1, wherein the body portion and the predetermined anatomical structure are one of the following:
   (i) the body portion includes the thyroid gland, and the predetermined anatomical structure is a trachea portion;
   (ii) the body portion includes a blood vessel and is a limb portion or a neck portion, and the predetermined anatomical structure is a bone portion or a muscle portion.

14. The method according to claim 1, wherein the relative tracking system includes at least one of an Inertial Measurement Unit (IMU) sensor, and image analysis of the ultrasound images, which is by a machine learning module having been trained to determine the relative three-dimensional motion between ultrasound image frames.

15. The method according to claim 1, wherein the relative tracking system is adapted for determining only relative motion between image frames of the first and second ultrasound image data.

16. The method according to claim 1, wherein the first and second partial volume images are segmented using a convolutional neural network.

17. The method according to claim 1, wherein the initial spatial relationship between the first and second partial volume images is established by a position aligning algorithm, the position aligning algorithm being configured for aligning
   the position of the predetermined anatomical structure in the first partial volume image and
   the position of the predetermined anatomical structure in the second partial volume image
   with each other, or with a position of the predetermined anatomical structure in the common volume,
   the position aligning algorithm is further configured for minimizing a spatial misalignment functional as a function of the spatial relationship between the first and second partial volume images, wherein the spatial misalignment functional further depends on the first and second anatomical structure position data.

18. The method according to claim 1, wherein the fine registration algorithm is a cross-correlation algorithm.

19. The method according to claim 1, further comprising applying an ultrasound decompression algorithm to the fine-registered spatial relationship.

20. The method of claim 1, wherein the three-dimensional classification output comprises a map of classification labels and/or probabilities as function of position in the first partial volume image and/or second partial volume image.

21. The method of claim 20, wherein the image segmentation creates a labeled volume image for the first partial volume image and a labeled volume image for the second partial volume image.

22. The method of claim 1, wherein the three-dimensional classification output indicates a position of the predetermined anatomical structure in the first partial volume image and/or the second partial volume image.

23. The method of claim 22, wherein the position of the predetermined anatomical structure in the first partial volume image and/or the second partial volume image comprises three coordinates indicating a position of a representative point of the predetermined anatomical structure.

24. The method of claim 23, wherein the representative point of the predetermined anatomical structure comprises a center of mass of the predetermined anatomical structure.

25. The method of claim 24, wherein the three-dimensional classification output further includes an orientation and/or a size of the predetermined anatomical structure.

26. An apparatus for generating a combined three-dimensional ultrasound image of a body portion, the apparatus comprising a relative tracking system and an ultrasound image combining system, wherein
   the relative tracking system is fixable to an ultrasound probe and is adapted for generating relative displacement data by monitoring the relative displacement of the ultrasound probe, and wherein
   the ultrasound image combining system comprises
      an input interface adapted for receiving first and second ultrasound image data generated by the ultrasound probe during a first and second ultrasound image acquisition, respectively, and first and second relative displacement data generated by the relative tracking module during the first and second ultrasound image acquisition, respectively;
      an image reconstruction module adapted for reconstructing a first and second partial volume image from the received first and second ultrasound image data and from the received first and second relative displacement data, respectively;
      an image segmentation module adapted for identifying first anatomical structure position data indicative of the position of the predetermined anatomical structure in the first partial volume image and for identifying second anatomical structure position data indicative of the position of the predetermined anatomical structure in the second partial volume image by image segmentation of the first and second partial volume image, respectively;
      an initial registration module adapted for establishing an initial spatial relationship between the first and second partial volume images in a common volume, based on the identified predetermined anatomical structure in the first and second partial volume images;
      a fine registration module adapted for adjusting the spatial relationship by a fine registration algorithm using the initial spatial relationship as an initial guess; and
      a combining module adapted for combining the first and second partial volume images in the common volume using the adjusted spatial relationship;
   wherein the relative tracking system is an inertial tracking using at least one from a group comprising an accelerometer and a gyroscope, and
   wherein segmentation of the first partial volume image and the second partial image volume comprises classifying voxels of the first partial volume image and the second partial image volume as one of multiple classes, either by probability maps or by a class label for each voxel, and outputs a three-dimensional classification output.

* * * * *